United States Patent [19]

Schwan et al.

[11] 4,063,022

[45] * Dec. 13, 1977

[54] ANTISECRETORY 2-IMIDAZOLIDINONES

[75] Inventors: Thomas J. Schwan; Nelson J. Miles, both of Norwich, N.Y.

[73] Assignee: Morton-Norwich Products, Inc., Norwich, N.Y.

[*] Notice: The portion of the term of this patent subsequent to Jan. 13, 1993, has been disclaimed.

[21] Appl. No.: 743,677

[22] Filed: Nov. 22, 1976

[51] Int. Cl.$^2$ ............................................. C07D 233/34
[52] U.S. Cl. ................................. 548/317; 424/273 R
[58] Field of Search ...................................... 260/309.7

[56] References Cited

U.S. PATENT DOCUMENTS

| 3,636,039 | 1/1972 | Gruenman et al. ............... 260/309.7 |
| 3,876,657 | 4/1975 | Aelony et al. .................... 260/309.7 |
| 3,932,452 | 1/1976 | Schwan et al. ................... 260/309.7 |
| 3,966,758 | 6/1976 | Schwan et al. ................... 260/309.7 |

OTHER PUBLICATIONS

Amos et al. Chem. Abst. 1962, vol. 56, cols. 2325–2326.
Baganz et al., Chem. Abst. 1965, vol. 63, col. 7008.
McKay, Chem. Abst. 1952, vol. 46, cols. 5583–5584.
van der Stelt et al., Chem. Abst. 1966, vol. 64, col. 15868.

*Primary Examiner*—Natalie Trousof
*Attorney, Agent, or Firm*—Anthony J. Franze

[57] ABSTRACT

(3,4-Substituted benzyl)-2-imidazolidinones are useful as gastric acid antisecretory agents.

3 Claims, No Drawings

ANTISECRETORY 2-IMIDAZOLIDINONES

This invention is concerned with compounds of the following formula which have utility in inhibiting gastric acid output and which find utility as medicinal agents:

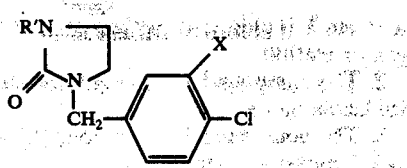

wherein X is chloro or trifluoromethyl and R' is hydrogen or methyl.

The methods currently preferred for preparing these compounds are illustrated in the following examples.

EXAMPLE 1

A. 1-(3,4-Dichlorobenzyl)-2-imidazolidinone

A 21.5 g (0.25 mole) portion of 2-imidazolidinone in 250 ml of dimethylsulfoxide was treated with 34.5 g (0.25 mole) of $K_2CO_3$, 10.0 g (0.06 mole) of KI and 49.0 g (0.25 mole) of 3,4-Dichlorobenzyl chloride. The reaction mixture was heated at 100° for 3 hours and poured into 1.8 l of $H_2O$. The aqueous mixture was extracted with 1.3 l of chloroform. The chloroform extract was washed with 500 ml of $H_2O$, dried over $MgSO_4$ overnight and filtered. The filtrate was concentrated to dryness to give 14 g (23%) of a light yellow semisolid. The crude product was crystallized using 20 ml of acetonitrile, filtered, washed with ether, air dried and dried at 60° for 2 hrs to give 10.5 g (17%) of a white solid, m.p. 129°-130°. An analytical sample, m.p. 129°-130°, was a portion of the above crystallized product.

Anal. Calcd. for $C_{10}H_{10}Cl_2N_2O$: C, 49.00; H, 4.11; N, 11.43. Found: C, 48.96; H, 4.06; N, 11.21.

B. 1-(3,4-Dichlorobenzyl)-3-methyl-2-imidazolidinone A 19.0 g (0.077 mole) portion of I-A in 260 ml of toluene was treated at 25°-30° over 0.2 hr with 5.6 g (0.14 mole) of sodium hydride (60% in mineral oil) using rapid stirring. The mixture was treated dropwise, while stirring, with 22.5 ml (0.36 mole) of methyl iodide at 25°-30° over 0.4 hr. The reaction mixture was stirred for 18 hrs. at ambient temperatures and treated cautiously with 250 ml of $H_2O$. The two phase system was separated and the aqueous layer was extracted with 250 ml of toluene. The toluene extracts were washed with 250 ml of water, dried over $MgSO_4$, filtered and concentrated to dryness under reduced pressure to give a viscous oil. The crude oily product was washed with 100 ml of heptane to remove the mineral oil giving 18.5 g (93%) of a colorless viscous oil which crystallized, m.p. 53°-55°. The crystallized product was again washed with 150 ml of warm heptane to give 14 g (70%, of a white solid, m.p. 53°-55°. An analytical sample, m.p. 54°-56°, was recrystalized from heptane.

Anal. Calcd. for $C_{11}H_{12}Cl_2N_2O$: C, 50.98; H, 4.67; N, 10.81 Found: C, 51.00; H, 4.65; N, 10.66

EXAMPLE II

A. 4-Chloro-3-trifluoromethylbenzyl alcohol

A 57 g (0.27 mole) portion of 4-chloro-3-trifluoromethylbenzadehyde in 400 ml of methanol was treated with 9 g (0.24 mole) of sodium borohydride at 0°-10° over 0.3 hr. The reaction mixture was stirred at room temperature for 3.5 hrs and filtered. The filtrate was concentrated under reduced pressure to give a solid residue which was partitioned between 250 ml of $H_2O$ and 250 ml of chloroform. The aqueous phase was again extracted with 250 ml of chloroform. The chloroform extracts were combined, washed with 100 ml of 10% hydrochloric acid, 100 ml of $H_2O$, dried over $MgSO_4$ and filtered. The filtrate was concentrated under reduced pressure to give 49 g (86%) of a brown-orange liquid which crystallized upon cooling, m.p. 26°-29°.

B. 4-Chloro-3-trifluoromethylbenzyl chloride

A 49 g (0.23 mole) portion of II-A in 320 ml of chloroform was treated with 75 ml (0.87 mole) of thionyl chloride over 0.3 hr at 0°-10° using rapid stirring. The reaction mixture was then allowed to warm to room temperature over 0.8 hr, heated to reflux, allowed to cool to room temperature over 1.5 hrs and filtered. The filtrate was concentrated under reduced pressure to give a viscous residue. The residue was taken up in 100 ml of toluene and again concentrated under reduced pressure to give 53 g (100%) of the desired product, a light brown oil.

C. 1-(4-Chloro-3-trifluoromethylbenzyl)-2-imidazolidinone

A. 28 g (0.33 mole) portion of 2-imidazolidinone in 150 ml of DMSO was treated with 22 g (0.16 mole) of $K_2CO_3$, 14 g (0.084 mole) of KI and 37.0 g (0.16 mole) of II-B. The reaction mixture was heated at 105°-110° for 1.6 hrs. The slurry was then treated with 250 ml of $H_2O$, stirred for 0.2 hr and extracted with four 125 ml portions of chloroform. The chloroform extracts were washed with 100 ml of $H_2O$, dried over $MgSO_4$ and filtered. The filtrate was then concentrated under reduced pressure to give 46 g of a light yellow oil. The oil was then washed with 500 ml of heptane and again concentrated under reduced pressure to give 41 g (91%) of a light yellow oil. This oil was then crystallized using 50 ml of ether, cooled and filtered. The white solid was washed with 15 ml of ether, air dried to a constant weight at 60°, m.p. 119°-121°. Yield: 7.0 g (16%).

Anal. Calcd. for $C_{11}H_{10}ClF_3N_2O$: C, 47.41; H, 3.62; N, 10.05. Found: C, 47.62; H, 3.59; N, 10.05.

The compounds described herein exhibit a salutary effect upon gastric acid secretion. Such effect is evidenced using a modified standard pyloruslighted secretory testing procedure in the rat. Sprague-Dawley rats, weighing 180°-210 g and previously fasted for 24 hrs, were used. All compounds were given perorally as suspensions in 0.5% Methocel 1 hr prior to pylorus ligation. Under light ether anesthesia, the rat stomach was ligated at the pylorus region. Four hrs after ligation the conscious rat was sacrificed by a chloroform overdose. The stomach was carefully excised and its content drained into a centrifuge tube. Samples were centrifuged to separate secretions from debris. Gastric fluid volume reading and determination of sample contamination, based on debris and sample color, was made. Titration was performed on a sample aliquot of 1 ml diluted to a volume of 5 ml using distilled water. The titrant used was 0.1N NaOH. Total gastric acid output in the stomach was determined by titration to ph 7. A dose of 300 mg/kg p.o. of a compound was administered to a group of rats and its effect on the volume of gastric secretion and acid output compared to a control group receiving 0.5% Methocel p.o. The activity of each compound based on the degree of inhibition of gastric acid output is set forth in Table I.

Table I
| Compound of Example | % of Control | |
| --- | --- | --- |
| | Gastric Acid Output | Vol. of Gastric Secretion |
| I-B | 8.9 | 39.2 |
| 11-C | 16.8 | 23.0 |
What is claimed is:
1. A compound of the formula:
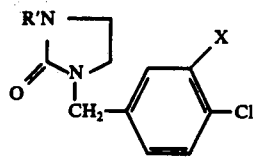
wherein X is chloro or trifluoromethyl and R' is hydrogen or methyl.
2. The compound 1-(3,4-dichlorobenzyl)-3-methyl-2-imidazolidinone.
3. The compound 1-(4-chloro-3-trifluoromelthylbenzyl)-2-imidazolidinone.
* * * * *